United States Patent
Sullivan

(10) Patent No.: US 7,228,165 B1
(45) Date of Patent: Jun. 5, 2007

(54) APPARATUS AND METHOD FOR PERFORMING A TISSUE RESECTION PROCEDURE

(75) Inventor: Roy Sullivan, Millville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1201 days.

(21) Appl. No.: 09/603,886

(22) Filed: Jun. 26, 2000

(51) Int. Cl.
*A61B 5/00* (2006.01)

(52) U.S. Cl. ............ 600/411; 600/414; 600/426; 600/427; 600/431; 606/167

(58) Field of Classification Search ........... 600/429, 600/407, 411, 424, 425, 427, 436, 414, 426, 600/431; 378/4, 21, 42, 62, 37; 601/2; 604/22; 606/167
See application file for complete search history.

(56) References Cited

U.S. PATENT DOCUMENTS

| | | | |
|---|---|---|---|
| 4,796,637 A * | 1/1989 | Mascuch et al. | 600/435 |
| 4,830,849 A * | 5/1989 | Osterholm | 435/4 |
| 5,482,040 A * | 1/1996 | Martin, Jr. | 600/407 |
| 5,485,839 A * | 1/1996 | Aida et al. | 600/427 |
| 5,772,594 A | 6/1998 | Barrick | 600/407 |
| 5,799,055 A | 8/1998 | Peshkin et al. | 378/42 |
| 5,843,000 A | 12/1998 | Nishioka et al. | 600/566 |
| 5,868,760 A * | 2/1999 | McGuckin, Jr. | 606/139 |
| 5,891,133 A * | 4/1999 | Murphy-Chutorian | 606/7 |
| 6,019,724 A | 2/2000 | Gronningsaeter et al. | 600/439 |
| 6,151,521 A * | 11/2000 | Guo et al. | 600/407 |
| 6,214,018 B1 * | 4/2001 | Kreizman et al. | 606/130 |
| 6,236,875 B1 * | 5/2001 | Bucholz et al. | 600/407 |

* cited by examiner

*Primary Examiner*—Ruth S. Smith
(74) *Attorney, Agent, or Firm*—Fay Kaplun & Marcin, LLP

(57) ABSTRACT

An apparatus and a method for performing a medical procedure is disclosed. In an embodiment for an apparatus of the present invention, the apparatus includes a positioning system and a resection device disposed within the positioning system. The positioning system includes an imaging device, a video processor coupled to the imaging device, a computer coupled to the video processor, and a video display coupled to the computer. In an embodiment for a method of practicing the present invention, the method includes the steps of creating an image of a lesion within a patient's body on an imaging device. Data representative of the lesion image is processed by a video processor. Tissue margins around the lesion are defined by a processor based on the processed data representative of the lesion image and a resection device is operated during a resection procedure within the patient's body based upon the defined tissue margins.

10 Claims, 3 Drawing Sheets

APPARATUS AND METHOD FOR PERFORMING A TISSUE RESECTION PROCEDURE

BACKGROUND OF THE INVENTION

1. Field of the Invention

The present invention relates generally to an apparatus and method for performing a medical procedure. More specifically, the invention provides for identifying target tissue margins and for guiding a tissue resection device to the target tissue in a tissue resection procedure.

2. Description of the Related Art

An endoluminal procedure is a medical procedure that takes place in one of the many tubes, or lumens, within the human body. The endoluminal procedures may take place in vascular, gastrointestinal, or air exchange lumens, and may involve disease diagnosis and/or treatment. Millions of endoluminal procedures are performed each year in hospitals around the world.

A procedure that is often carried out endoluminally is the removal of "suspect" or diseased tissue. The purpose of such tissue removal, or resection, may be to provide tissue samples for histological analysis or removal of diseased tissue as a treatment means. Today, endoluminal resection of tissue is often done using only the subjective judgment of the clinician to determine where tissue should be removed. As disease tissue margins are sometimes difficult to determine visually, tissue resection guided solely by visual cues can be inaccurate and even dangerous. The danger arises when resectioning cancerous tissues that are prone to metastasize. In this case, a tissue resection that occurs without sufficient buffer of healthy tissue risks leaving behind cancerous tissue requiring repeated resectioning procedures, or worse, causing the cancerous lesion to "seed", or metastasize, to other parts of the body.

FIGS. 1 and 2 illustrate a prior art endoluminal device 100 that could be used in the harvesting of diseased tissue from within a body lumen. The device is comprised of a flexible catheter body 110 with a proximal end 112 and distal end 114. At the proximal end 112 there is a suction adjust knob 120, a coupler 130, a vacuum hose 140, head-actuating handle 150, and an electrical interconnect 160. The vacuum hose 140 makes connection from a vacuum pump 142, through the coupler 130, to a central lumen 170 within the catheter body 110 to draw a suction on tissue-harvesting chamber 190. The electrical interconnect 160 is comprised of electrical leads 161 that pass from the external electronics 162, through the coupler 130 at the proximal end 112 of the catheter body 110 to a cavity 116 outside the central lumen 170 but within the catheter body 110. Some of the electrical leads 161 supply electrical energy to a light source 163 and a vision chip 164 situated at the distal end 114 of the catheter 110, while another group of the electrical leads 161 bring electrical signals from the vision chip 164 to a video processor and a display device 165. The head-actuating handle connects to a cable (not shown) that travels the length of the catheter body 110 within the central lumen 170 to control the operation of the endoluminal device's head assembly 180.

FIG. 2 is a detailed view of the distal end 114 of the device 100 of FIG. 1. At the distal end 114 of the catheter body 110 there is a head assembly 180, a tissue-harvesting chamber 190, a cutting device 192, and the light source 163 and the vision chip 164. The tissue-harvesting chamber 190 is connected to the central lumen 170 of the catheter body 110. The central lumen 170 is connected to the external vacuum pump 142. The head assembly 180 is movable with respect to the catheter body 110 and, thus, can be extended or retracted using the cable that is attached to the head-actuating handle 150 at the proximal end 112 of the device 100 and to the head assembly 180 at the distal end 114 of the device 100. The cutting device 192 is a sharpened blade that severs the tissue 200 as the retracting head assembly 180 presses the tissue 200 against the cutting device 192 to remove the suspect tissue area 210. Distal end 114 also includes staples 194 and anvil surface 196 which are utilized to staple the site. The vision chip 164 is connected to the external video processor and display device 165 via the electrical leads 161 within the catheter body 110, but outside of the central lumen 170.

FIG. 2 also illustrates the distal end 114 of the prior art tissue-resectioning device 100 as it would appear having been inserted into a body lumen. Extended into the body lumen, the Endoscopist would guide the distal tip 114 of the device into close proximity with the tissue 200 to be resected. By adjusting the suction at the tip 114 with the suction adjust knob 120, the clinician can then increase the suction at the tip 114 until the tissue 200 is drawn into the tissue harvesting chamber 190 through a distal opening 114A and into the tissue harvesting chamber 190. Once the tissue is in position, the clinician can then retract the head assembly 180 to perform the resection. The suspect tissue 210 is removed and the site is stapled with the staples contained in the head assembly 180. With the tissue sample 210 enclosed within the tissue-harvesting chamber 190, the device 100 can be removed from the body lumen and the tissue sample 210 removed.

Today, a tissue-resectioning procedure such as described above would be guided by the clinician based upon whatever limited visual information could be obtained through the vision chip 164 at the distal end 114 of the catheter 110. Whereas histological staining may be used to assist in tissue margin identification, guiding the resection device 100 in the procedure in this manner is still a very subjective process and prone to error. There is a high probability that either too much or too little tissue will be resected. Both of the outcomes are undesirable, and even dangerous.

Therefore, it would be desirable to provide an improved system and method for assisting a practitioner in accurately identifying target tissue margins and guiding the practitioner to the target tissue.

SUMMARY OF THE INVENTION

An apparatus and a method for performing a medical procedure is provided. In an embodiment for an apparatus of the present invention, the apparatus includes a positioning system and a resection device disposed within the positioning system. The positioning system includes an imaging device, a video processor coupled to the imaging device, a computer coupled to the video processor, and a video display coupled to the computer. In an embodiment for a method of practicing the present invention, the method includes the steps of creating an image of a lesion within a patient's body on an imaging device. Data representative of the lesion image is processed by a video processor. Tissue margins around the lesion are defined by a processor based on the processed data representative of the lesion image and a resection device is operated during a resection procedure within the patient's body based upon the defined tissue margins.

BRIEF DESCRIPTION OF THE DRAWINGS

The various features of the invention will best be appreciated by simultaneous reference to the description which follows and the accompanying drawings, in which.

DETAILED DESCRIPTION

Figure 3:
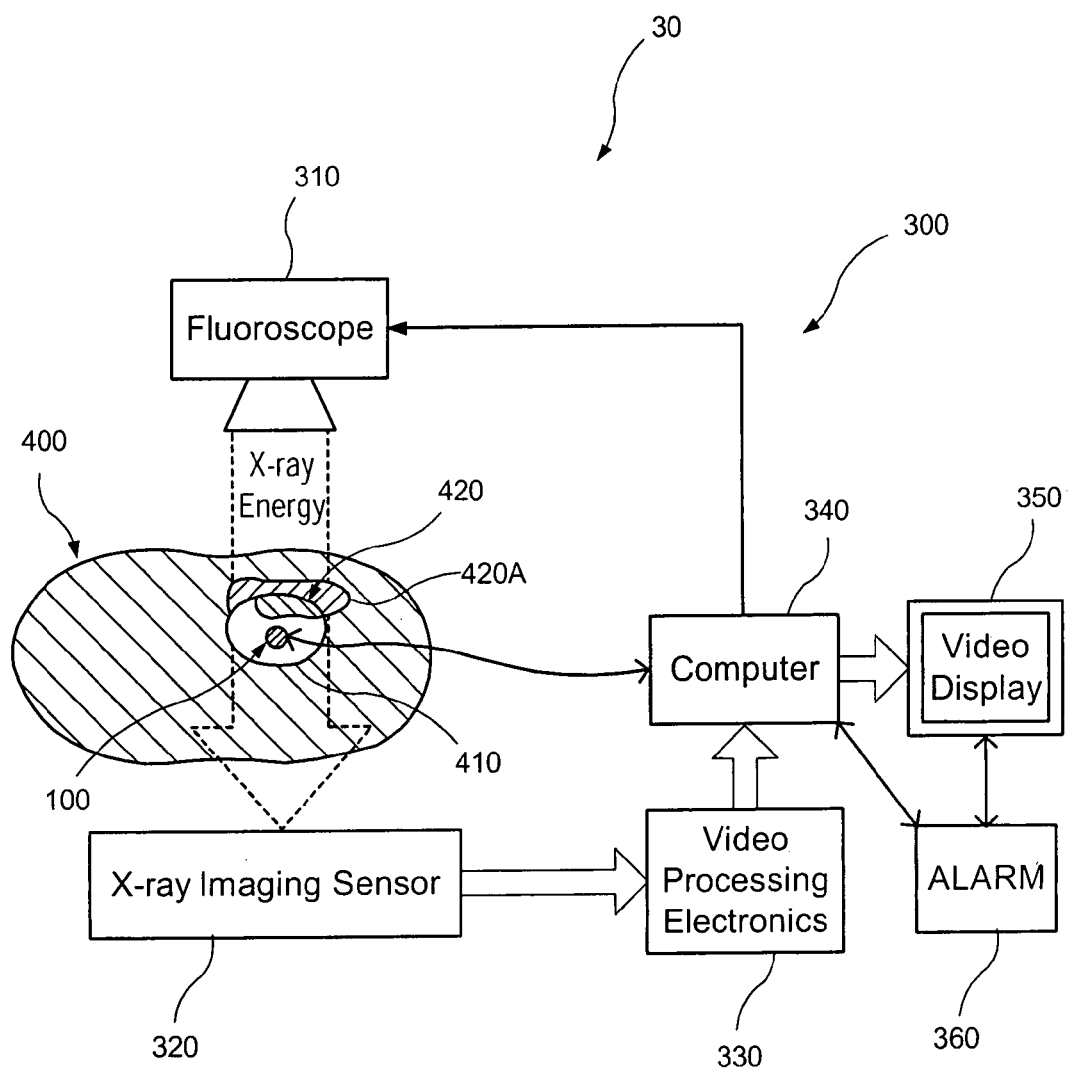
FIG. 3 is an embodiment of a system for performing a medical procedure in accordance with the principles of the present invention.

FIG. 3 illustrates an embodiment of a system for performing a medical procedure in accordance with the principles of the present invention. As can be seen in FIG. 3, the system 30 includes a positioning system 300 and a resection device 100. In the illustrated embodiment, the positioning system 300 includes a fluoroscope 310, an x-ray imaging sensor 320, video processing electronics 330, a computer 340, a video display 350, and an alarm 360. As can be further seen in FIG. 3, the system 30 further includes a resection device 100 that is positionable within the positioning system 300. Resection device 100, as is well-known in the art, can be utilized to remove an internal lesion 420 from a tubular organ 410 within a body wall 400 of a patient and resect the tissue of the tubular body organ 410 from which lesion 420 is removed. As will be further explained later in this specification, fluoroscope 310 generates x-rays that are detected by the x-ray imaging sensor 320. The x-rays generated by fluoroscope 310 pass through the patient and lesion 420 to be collected on x-ray imaging sensor 320. A radiopaque die, having selectively been absorbed by lesion 420, creates an image of the boundaries of lesion 420 on x-ray imaging sensor 320. Image information from x-ray imaging sensor 320 related to lesion 420 is communicated to video processing electronics 330 where the video processing electronics processes the image information from sensor 320 and provides digitized image data to computer 340. Computer 340 utilizes the digitized image data to identify a tissue margin 420A around lesion 420. The tissue margin 420A is provided to video display 350 where the tissue margin can be displayed relative to lesion 420.

In addition to computer 340 receiving position image data for lesion 420 from x-ray imaging sensor 320, computer 340 is also able to receive position image data for resection device 100. Thus, computer 340 is able to provide relative positioning data for resection device 100, lesion 420, and the defined tissue margin 420A.

Through use of the present system 30, if, during the resection procedure, the resection device, through operation by the surgeon, is in danger of severing tissue outside of tissue margin 420A or is in danger of not removing a sufficient amount of tissue surrounding lesion 420, as defined by tissue margin 420A, computer 340 is able to provide an alarm to alarm device 360 to alert the physician that is performing the procedure of the particular situation.

Thus, through utilization of system 30, the physician is able to objectively determine the amount of tissue that is to be removed when preforming the procedure. This provides advantages over the currently known methods and apparatuses that are utilized by surgeons who perform these procedures. As discussed previously, today, a tissue-resectioning procedure is guided by the surgeon based on whatever limited visual information is obtainable through the vision system located at the distal end of the resection catheter. Guiding the resection procedure in this manner is a very subjective process and prone to error, with a danger of taking either too much or too little tissue from around the lesion to be removed.

In further describing the present invention, as described previously, fluoroscope 310 is utilized to generate x-rays that are directed through the patient's body and, thus, through lesion 420. Whereas the present invention is described as utilizing an imaging device which consists of a fluoroscope, 310 and an x-ray imaging sensor 320, any of a variety of different imaging devices may be utilized in practicing the principles of the present invention. For example, a magnetic resonance imaging device (MRI) could be utilized in the present invention to provide an image of lesion 420 and resection device 100. Thus, the present invention is not limited to utilizing a fluoroscope and x-ray energy in practicing the present invention.

As described previously, lesion 420 absorbs a radiopaque die which creates an image of the lesion on the x-ray imaging sensor 320 when lesion 420 is radiated by the x-rays emitted from fluoroscope 310. The radiopaque die may be administered to lesion 420 through any of a variety of procedures and the present invention is not limited to any particular procedure for introducing the radiopaque die within lesion 420. For example, the die could be administered either intravenously or topically to the lesion site. Similarly, the operating end, or distal end, of resection device 100 could also contain a radiopaque die on it. This would also allow for the position of the resection device to be detected by the x-ray imaging sensor 320 when radiated by fluoroscope 310.

X-ray imaging sensor 320 detects the x-rays generated by fluoroscope 310 and is thus able to create an image of lesion 420 and resection device 100. Image information detected by x-ray imaging sensor 320 for both lesion 420 and resection device 100 is provided to video processing electronics 330. Video processing electronics 330 processes the image information received from imaging sensor 320 and provides this processed, digitized image data to computer 340.

Computer 340 may be any of a variety of processing devices that are capable of processing electronic information, either in a digital or analog format. For example, computer 340 could be a personal computer. Computer 340 contains software that is able to define a tissue margin 420A around lesion 420. As described previously, tissue margin 420A defines a sufficient area of tissue around lesion 420 such that if the surgeon removes lesion 420 and the tissue surrounding lesion 420 defined by tissue margin 420A, enough tissue is removed from around lesion 420 to help ensure that all of the diseased tissue is removed from body organ 410. Additionally, removal of the surrounding tissue defined by tissue margin 420A also helps to ensure that too much healthy tissue is not removed from body organ 410. Thus, computer 340 defines the tissue margin that is to be removed from a tubular body organ when removing a lesion from the tubular organ during a resection procedure.

As described previously, computer 340 is provided with digitized image data of lesion 420 within body organ 410 such that computer 340 is able to determine the position, and thus the boundaries, of lesion 420 within tubular body organ 410. By knowing the position of lesion 420 within body organ 410, computer 340 is able to define tissue margin 420A around lesion 420. Any number of different methodologies may be utilized to define tissue margin 420A around lesion 420 and the present invention is not limited to any particular methodology. All that is required is that an objectively determined tissue margin is defined around the lesion to be removed such that the surgeon performing the procedure is able to perform the procedure while considering the defined tissue margin.

An exemplary methodology for determining tissue margin 420A around lesion 420 is to utilize a pre-selected absolute measure of tissue. For example, computer 340 could define tissue margin 420A such that the tissue margin consists of a one-inch boundary of tissue extending from the outer boundaries of lesion 420. Alternatively, computer 340 could define tissue margin 420A as being a measure of tissue that is a pre-selected percentage of a physical dimension of lesion 420. For example, if lesion 420 has a thickness of one-inch, computer 340 could define the tissue margin 420A such that the margin extends 100% of the thickness of lesion 420 from the outer boundaries of lesion 420, which in this example would result in a one-inch tissue margin. Thus, tissue margin 420A would be defined to encompass a boundary of one-inch of tissue that surrounded lesion 420.

Whereas two alternative methodologies for defining tissue margin 420A are provided above, as stated previously, any number of methodologies can be utilized for defining tissue margin 420A and the present invention is not limited to any particular methodology. Computer 340 may utilize any methodology for defining a tissue margin around a lesion based on the image data of the lesion received from the video processing electronics. The surgeon performing the procedure may selectively set the parameters for defining the tissue margin, based upon considerations of the particular procedure being performed, by inputting the parameters' definitions into computer 340.

Once computer 340 has defined tissue margin 420A around lesion 420, computer 340 provides this defined tissue margin 420A to video display 350. Video display 350 displays the lesion 420, the defined tissue margin 420A around the lesion, and the position of resection device 100. Thus, video display 350 provides a visual presentation that the surgeon can monitor while performing the resection procedure and can utilize to operate the resection device 100 such that sufficient tissue defined by tissue margin 420A is removed when removing lesion 420. Whereas video display 350 is illustrated as being a separate element from computer 340, the video display may be integrated into the computer and, thus, separate structural elements are not required for these components.

One methodology that the surgeon can utilize when practicing the present invention is to visually observe the defined tissue margin 420A around lesion 420 when operating resection device 100. The surgeon is able to remove the proper amount of tissue from tubular organ 410 by visually observing the lesion 420, the defined tissue margin 420A, and the resection device 100 when performing the resection procedure. By visually observing the position of the resection device 100 relative to the lesion 420 and tissue margin 420A during the procedure, the surgeon can ensure that the proper amount of tissue, as defined by tissue margin 420A, is removed from the tubular organ.

Because computer 340 is also detecting the position of resection device 100 as resection device 100 is performing the procedure, if the resection device 100 is operated by the surgeon such that the surgeon is either taking too much tissue or not taking enough tissue, as defined by tissue margin 420A, computer 340 can provide an alarm to alert the surgeon of the error. Computer 340 is coupled to alarm device 360 and may provide either an audible alarm that will sound on alarm device 360 or could provide a signal to alarm device 360 which would be visually displayed on video display 350. Thus, as the surgeon is watching the video presentation of the procedure on video display 350, if the surgeon is operating resection device 100 such that it is not removing tissue as defined by tissue margin 420A, an alarm can be provided to alert the physician of this error.

Whereas the above embodiment describes a component for generating an alarm, i.e., alarm device 360, that is a separate component, it is not required that the alarm function be performed by a component separate from either computer 340 or video display 350. The principles of the present invention may be practiced by including the functionality of the alarm device in either computer 340 and/or video display 350. Thus, the alarm function can be performed by a software module contained in any of the other components of the present invention.

In continuing with the description of the methodologies of the present invention, as described above, the surgeon performing the procedure may visually monitor video display 350 to control his or her operation of resection device 100. Alternatively, as is illustrated in FIG. 3, computer 340 can also be directly coupled to resection device 100. Thus, computer 340 can directly control resection device 100. For example, rather than having to rely on the surgeon visually monitoring the position of resection device 100 with respect to the defined tissue margin 420A on video display 350, if computer 340 detects an error in the physician's positioning of resection device 100 outside of defined tissue margin 420A, i.e., too much tissue is being removed, computer 340 could be programmed to disable resection device 100 in this situation. Thus, if computer 340 determines that resection device 100 is being operated such that tissue outside of defined tissue margin 420A is being removed, computer 340 can provide a signal to resection device 100 to disable resection device 100. For example, the resection device could be disabled such that its head assembly could not be opened to receive tissue within it, and/or the cutting blade could be retracted such that it could no longer cut tissue, and/or the suction could be disabled, and/or head-actuating handle 150 could be disabled. These, or any of a variety of other methodologies, could be utilized to disable resection device 100. Thus, due to computer 340 disabling resection device 100 if the resection device is mis-positioned, the physician is not physically able to remove too much tissue from around lesion site 420. In addition to disabling resection device 100 in this circumstance where too much tissue is about to be removed, computer 340 could also provide the visual and/or audible alarms as previously described.

Whereas it was described above that computer 340 disables resection device 100 if too much tissue was being removed, computer 340 could also disable resection device 100 if too little tissue was also being removed.

As described above, in an embodiment of the present invention, computer 340 is able to control the operation of resection device 100 by monitoring the positions of the resection device 100, the lesion 420, and the defined tissue margin 420A around lesion 420.

As is further illustrated in FIG. 3, computer 340 can also be coupled to fluoroscope 310. Thus, based on the quality of the image data received by computer 340 from video processing electronics 330, computer 340 may control fluoroscope 310 in order to receive a better quality of image data. Computer 340 can control fluoroscope 310 in order to attempt to obtain better quality image data by any of a variety of different methodologies. For example, computer 340 could physically alter the positioning of fluoroscope 310 such that better quality image data is received or computer 340 could alter the x-ray dosage delivered by fluoroscope 310. Thus, computer 340 is able to control fluoroscope 310 in order to provide image data of a higher quality than that possibly originally received from video processing electronics 330.

Thus, as described above, the apparatuses and methods of the present invention can be utilized by a surgeon to guide the surgeon in the resectioning procedure. With knowledge of the objectively-defined tissue margins of the lesions, the system monitors the position of the resectioning catheter relative to the tissue margins and warns the surgeon, through either audible alarms and/or visual queues on a video monitor, if either too much or too little healthy tissue is being taken. In another embodiment of the invention, as described above, the system is able to control the resectioning catheter, preventing it from cutting unless proper tissue margins are being maintained.

Whereas fluoroscopy has been previously known in assisting surgeons to visualize a treatment site during orthopedic surgery, it is not known to use such a system with a resection procedure. The present invention is able to safely reduce the amount of healthy tissue that is resected with the diseased tissue while it increases the chances of resecting the entire lesion in a single procedure so that repeat procedures are not necessary. This reduces cost and discomfort to the patient as well as reducing the chances for metastasis of cancerous tissue by reducing the amount of damage to the lesion during its resection.

Whereas the previously described embodiments of the present invention would possibly provide a two-dimensional image, it is also possible within the present invention to add a secondary imaging device, e.g., a second x-ray source, and combine the data of the two x-ray sources to create 3-D imagery. U.S. Pat. Nos. 5,772,594 and 5,799,055 describe fluoroscopy in medical procedures and are incorporated herein by reference.

Figure 1:
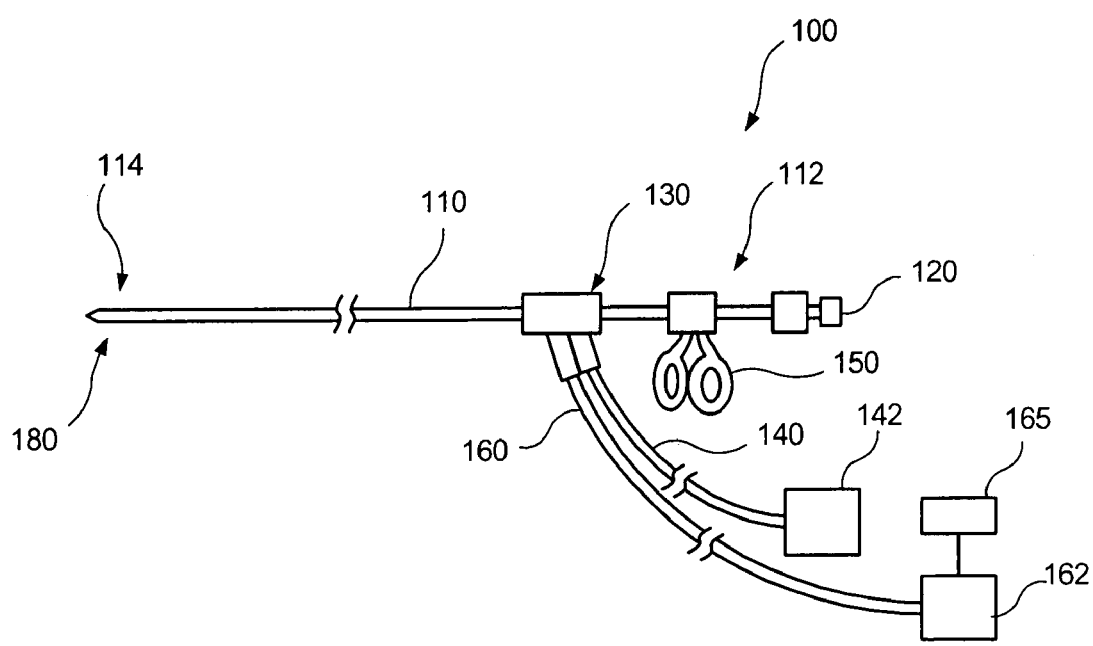
FIG. 1 illustrates a known endoluminal device.
Figure 2:
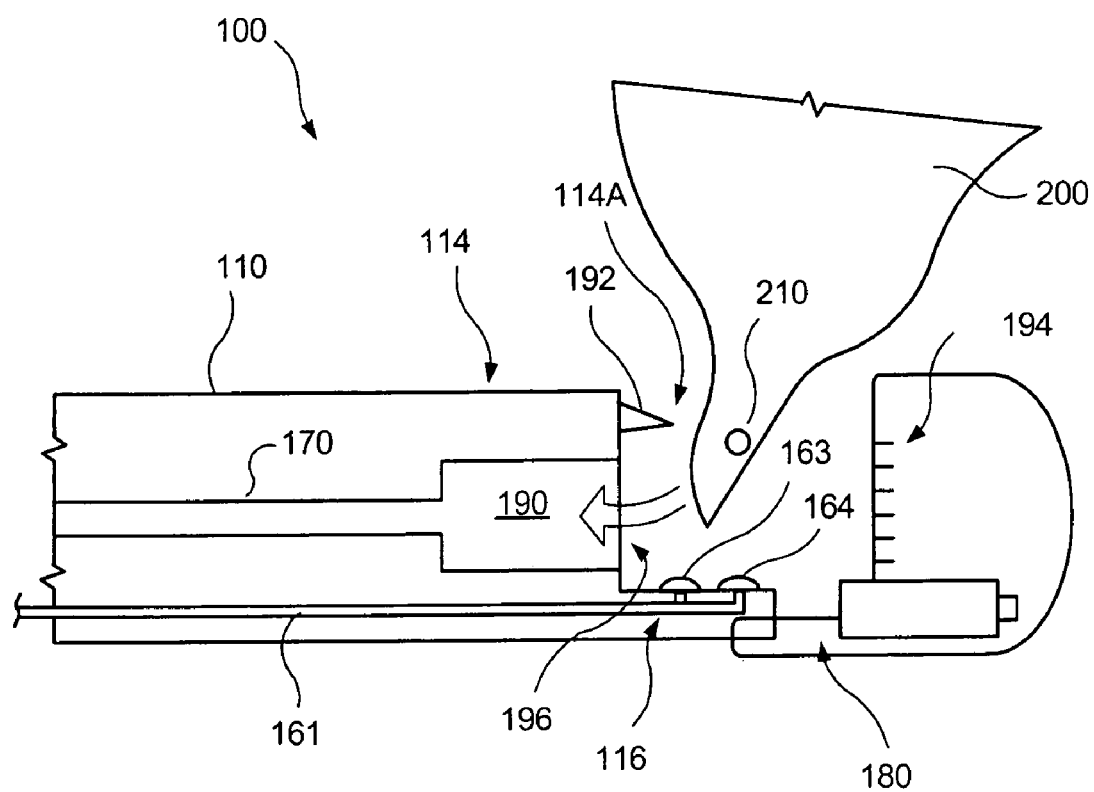
FIG. 2 is a detailed view of the distal end of the device of FIG. 1.

The apparatuses and methods of the present invention can be utilized with any of a variety of different resection devices and the present invention is not limited to any particular resection device in practicing the present invention, including the embodiment described in FIGS. 1 and 2 with or without the vision chip and light source. For example, a resection device as described in U.S. Pat. No. 5,868,760, which is incorporated herein by reference, may be utilized when practicing the present invention. Additionally, the resection device described in Ser. No. 09/100,393 filed on Jun. 19, 1998, now issued as U.S. Pat. No. 6,126,058, which is also incorporated herein by reference, could also be utilized when practicing the present invention. Again, any of a variety of known resection devices can be utilized in the present invention.

More specifically, the present invention may be utilized with a flexible endoscopic resection system including a flexible endoscope slidably received through at least a portion of a stapling mechanism comprising an anvil and a stapling head mounted to the anvil so that the anvil and the stapling head are moveable with respect to one another between a tissue receiving position and a stapling position. A position adjusting mechanism is provided for moving the anvil and the stapling head between the tissue receiving and stapling positions and a staple firing mechanism sequentially fires a plurality of staples from the stapling head across the gap against the anvil and through any tissue received in the gap and a knife cuts a portion of tissue received within the gap. A control unit which remains outside the body is coupled to the stapling mechanism for controlling operation of the position adjusting mechanism and the staple firing mechanism. The endoscope is inserted into a naturally-occurring body orifice to locate a lesion, for example, in a tubular organ under visual observation (usually while insufflating the organ). Once the lesion has been located, a working head assembly including a stapling mechanism and an anvil is slidably advanced along the endoscope into the tubular organ until the working head assembly is in a desired position adjacent to the lesion. Alternatively, the working head assembly may be detachably coupled to a distal end of the endoscope, and the entire arrangement may then be inserted into the body orifice under visual observation.

The disclosed embodiments are illustrative of the various ways in which the present invention may be practiced. Other embodiments can be implemented by those skilled in the art without departing from the spirit and scope of the present invention.

What is claimed is:

1. A tissue resectioning system, comprising:
    a resection head mounted at a distal end of an elongate flexible body, the resection head including a marker thereon wherein, when in an operative position, the resection head is located within a body lumen with the elongate flexible body extending through the body lumen to a naturally occurring body orifice;
    an imager which remains outside the patient's body, the imager generating image data of a selected region within the patient's body including a predetermined portion of tissue marked for resection;
    an image processing unit analyzing the image data to define a region of tissue to be resectioned and to locate the marker; and
    a control unit controlling the resection head based on the defined region of tissue and the location of the marker to resect the region of tissue.

2. The system according to claim 1 wherein the imager includes a fluoroscope and an x-ray imaging sensor.

3. The system according to claim 1 wherein the marker is radiopaque.

4. The system according to claim 1 wherein the defined region of tissue and the location of the marker are displayed on a video display coupled with the control unit.

5. The system according to claim 1 wherein the control unit disables the resection head if the marker indicates that the resection head is oriented outside the defined region of tissue.

6. The system according to claim 1 further comprising an alarm device wherein the control unit transmits an alarm signal to the alarm device when the marker indicates that the resection head is oriented outside the defined region of tissue.

7. The system according to claim 6 wherein the alarm device generates a visual alarm.

8. The system according to claim 1 wherein the imager is a magnetic resonance imager.

9. The system according to claim 1 wherein the image processing unit determines the defined region of tissue by an absolute measure of tissue.

10. The system according to claim 1 wherein the image processing unit determines the defined region of tissue by a percentage of a physical dimension of the lesion.

* * * * *